(12) United States Patent
Nosrati

(10) Patent No.: US 9,357,939 B1
(45) Date of Patent: Jun. 7, 2016

(54) METHOD AND APPARATUS FOR A SELF-PROGRAMMABLE WIRELESS MEDICAL MONITORING DEVICE

(71) Applicant: Farhad David Nosrati, Encino, CA (US)

(72) Inventor: Farhad David Nosrati, Encino, CA (US)

( * ) Notice: Subject to any disclaimer, the term of this patent is extended or adjusted under 35 U.S.C. 154(b) by 63 days.

(21) Appl. No.: 14/242,869

(22) Filed: Apr. 2, 2014

(51) Int. Cl.
*A61B 5/00* (2006.01)
*A61B 5/0432* (2006.01)
*A61B 5/0476* (2006.01)
*A61B 5/0488* (2006.01)

(52) U.S. Cl.
CPC ........... *A61B 5/04325* (2013.01); *A61B 5/0006* (2013.01); *A61B 5/0476* (2013.01); *A61B 5/0488* (2013.01)

(58) Field of Classification Search
USPC ........................................................ 600/516
See application file for complete search history.

(56) References Cited

U.S. PATENT DOCUMENTS

| | | | |
|---|---|---|---|
| 5,511,553 A | 4/1996 | Segalowitz | |
| 6,453,186 B1 | 9/2002 | Lovejoy | |
| 6,496,705 B1 | 12/2002 | Ng | |
| 6,987,965 B2 | 1/2006 | Ng | |
| 7,171,166 B2 | 1/2007 | Ng | |
| 7,206,630 B1 | 4/2007 | Tarler | |
| 8,290,574 B2 | 10/2012 | Feild | |
| 8,433,399 B1 | 4/2013 | Nosrati | |
| 8,560,054 B2 | 10/2013 | Badilini | |
| 8,639,319 B2 | 1/2014 | Hugh | |
| 2009/0005675 A1* | 1/2009 | Grunwald | A61B 5/042 600/424 |
| 2009/0105785 A1* | 4/2009 | Wei | A61N 1/36132 607/48 |

* cited by examiner

Primary Examiner — Nicole F Lavert

(57) ABSTRACT

A self-programmable Medical Monitoring system capable of adapting its monitoring and detection algorithms to each individual patient. The Monitoring device is further capable of uploading new detection algorithms as well as software applications from outside computing devices. Uploaded software applications can configure the Medical Monitoring device for additional applications including but not limited to an ECG, EEG and EMG device. The Monitoring device can operate as stand-alone device or it can communicate wirelessly with one or more outside computing devices.

16 Claims, 10 Drawing Sheets

SELF-PROGRAMMABLE MEDICAL DEVICE (SPMD)
HARDWARE ARCHITECTURE

SELF-PROGRAMMABLE MEDICAL DEVICE (SPMD)
HARDWARE ARCHITECTURE

SELF-PROGRAMMABLE MEDICAL DEVICE (SPMD)
SOFTWARE FLOW DIAGRAM

APPLICATION MANAGEMENT
DETAIL SOFTWARE FLOW DIAGRAM

LEVEL-2
ABNORMALITY ANALYSIS
300

LEVEL-3
NEW ALGORITHM GENERATION
400

METHOD AND APPARATUS FOR A
SELF-PROGRAMMABLE WIRELESS
MEDICAL MONITORING DEVICE

BACKGROUND OF INVENTION

1. Field of the Invention

The present invention relates to self-programmable wireless medical devices. In particular, the present invention relates to a self-programmable wireless medical device with a built-in intelligence to learn and to self-adapt its monitoring capabilities to an individual patient's needs. Furthermore, the present invention is capable of uploading various software applications from outside computing devices, enabling it to adapt its monitoring capabilities to a wide range of medical applications. Among these medical monitoring applications are included a self-programmable wireless electrocardiogram (ECG) device as well as a self-programmable wireless electroencephalogram (EEG) device and a self-programmable wireless electromyogram (EMG). The ECG monitoring system and its novel innovations are described here in details.

The present invention further relates to a self-programmable wireless electrocardiogram (ECG) monitoring system. More specifically, the present invention relates to an ECG monitoring system with a built-in intelligence to learn and self-adapt its monitoring capabilities to an individual patient's needs. The ECG device continuously records and monitors the patient's cardiovascular activity to identify and extract various parameters that are then utilized to further optimize the built-in arrhythmia detection algorithms. The optimized algorithms are then uploaded for future monitoring purposes. In the event that an abnormal event is detected, the recorded cardiovascular data leading to and prior to the abnormal event is then scrutinized to further optimize the detection algorithms being used on this patient. Optimized detection algorithms and parameters are then uploaded and activated for all future monitoring of the patient. The ECG device is further capable of performing image recognition and overlay techniques using historical recordings to further optimize its monitoring capabilities and identify "trends" in patient's heart activity. In one configuration, the ECG unit can communicate the recorded cardiovascular data wirelessly to outside computing devices for further analysis and monitoring purposes. The ECG monitoring device can be mounted on disposable media such as a patch for ease of use and added comfort. The ECG device is capable of uploading software applications and detection algorithms enabling it to further adapt itself to new applications including but not limited to electroencephalogram (EEG) and electromyogram (EMG).

2. Description of Prior Art

ECG systems are used for monitoring activity of a patient's heart. A number of electrodes are positioned on the patient. Wires are connected from the electrodes to an ECG monitor. The ECG monitor processes the signals and outputs ECG data, in form of traces representing activity of the heart by measuring electrical signals at different positions on the patient.

Several classes of ECG monitoring devices are presently available in the market. Each of these devices exhibits major issues and limitations that the current invention resolves.

The most common class of ECG monitoring devices are stand-alone ECG monitoring systems which are generally used to monitor and record patient's cardiovascular activity within a hospital or clinic environment and display or print the resulting waveforms for a doctor's viewing. One fundamental problem is that the wires of these devices inhibit movement by and around the patient. Because the patient is wired to the stationary ECG device, doctors must work around the wires to gain access to the patient.

Additionally, there are classes of ECG devices that are portable monitoring devices that do not connect the patient to an external stand-alone device. However, these, like their stand-alone counterparts have numerous shortcomings. Many of the prior art portable ECG monitoring devices are intended to be recording devices only. These devices record cardiovascular data over long periods of time for later viewing and analysis. Additionally, these devices are incapable of performing any type of analysis of the patient's cardiovascular condition. These devices are not interactive and are not remotely self-programmable. An example of such devices is the ubiquitous Holter ambulatory ECG monitor. This device is worn typically around the neck of the patient and is about the size of a tape recorder. From the bottom of the Holter monitor are several wires, generally five, that attach to electrodes that are placed about the patient's torso by sticky pads. Holter monitors continuously record a patient's ECG waveform over an extended period of time such as a 24-hour period or several weeks. These devices often contain a large storage memory for recording the patient heart waves over these long time periods. The patient carries the complete monitor and recorder. The Holter ECG devices record the cardiovascular data only; they cannot scrutinize the data, they merely save it for the primary care physician to review later. The data recorded by a Holter monitor is known and can be analyzed only after the recording period is over; therefore, if the patient experiences an abnormality, the Holter device is incapable of performing an immediate analysis or of assisting the patient by interactively communicating with a doctor. Additionally, Holter monitors lack the processing power and the necessary software algorithms to immediately analyze the ECG data.

Another class of ECG devices are portable extended-wear ECG monitoring devices, some of which store the recorded heart information and, in some cases, transmit that information wirelessly, to a local base station which relays the ECG data by phone to a diagnostic center where it can be promptly scrutinized for arrhythmias. However, this method constrains the normal daily activities of the patient, as the patient must continually stay within range of the local base station. Additionally, these devices don't perform any analysis nor are they self-programmable or adaptable to the patient's unique monitoring needs. Of those devices that are capable of some sort of analysis, such analysis is very limited and fixed. They cannot do any in-depth analysis and because they have fixed programs, they cannot upload or download software and algorithms that customize the detection, analysis and reporting for the patient's unique and individual needs.

Furthermore, among the portable extended-wear ECG monitoring devices, there are those that take the form-factor of a patch with adhesive contact to be placed directly on the patient's chest. These include both the disposable single-use ECG patches as well as the reusable type. Such patches are utilized by Holter monitors to simply record cardiovascular data over a period of time for future analysis by the physician. This group of portable ECG devices provides a higher level of comfort to the patient being monitored over a long period of time; however they lack the ability to transmit the recorded information wirelessly to outside devices. Once the recording period has elapsed, the device's contents are then analyzed by the physician.

Another class of ECG monitoring devices are portable extended-wear ECG monitoring devices capable of recording cardiovascular activity, transmitting that information wirelessly to an outside computing device, wherein said computing device makes this information available for a physician's review and analysis on the recorded cardiovascular data. However due to their limited processing power and their fixed built-in arrhythmia detection algorithms contained in their internal storage area, such patches are also very limited in their scope and accuracy in detection of abnormal heart activity.

Another class of ECG monitoring devices are portable extended-wear ECG monitoring devices that are equipped with the capability of analyzing and scrutinizing the patient's cardiovascular data for arrhythmia and other abnormal heart conditions.

Another class of ECG monitoring devices is wireless portable extended-wear ECG monitoring devices that work interactively with outside computing devices in order to optimize their detection algorithms. Such devices communicate to the outside commuting device the recorded patient cardiovascular information leading to each abnormal event via telemetry. The recorded information is then scrutinized by the outside computing device in order to generate more effective detection algorithms to be uploaded back into the portable ECG monitoring device. What is lacking in such devices is the ability to self-program and improve built-in detection algorithms without the aid of outside computing devices.

Most of the above classes of ECG monitoring devices can have the form-factor of a patch.

What is needed is an ECG device that has the capability to record the patient cardiovascular activity over an extended time period, such as a 24-hour period or longer, in conjunction with the ability to transmit the recorded data automatically or on-demand to an outside wireless computing device. Furthermore, there is a significant need for a wireless ECG monitoring device that is capable of analyzing and scrutinizing the patient's cardiovascular data for arrhythmia and other abnormal heart conditions. Also, in the event that abnormal activity or activities are detected, there is a significant need for an ECG monitor that can optimize its built-in detection algorithms to each patient's unique requirements by analyzing the recorded heart data leading to each abnormal event and extracting essential ECG parameters, without requiring any human assistance or interactions with outside computing devices. Additionally, there is a vital need for an ECG device that can process current as well as historical heart recordings to help identify "trends" in the patient's cardiovascular health. Furthermore, there is a need for an ECG device capable of uploading new application software both via local connection, as well as via telemetry, to help improve its performance and help expand its detection capabilities in other fields including but not limited to electroencephalogram (EEG), electromyogram (EMG), blood pressure, oxygen levels and the like. The present invention provides all of the above capabilities and corrects the deficiencies of the prior art.

SUMMARY OF THE INVENTION

The present invention relates to a self-programmable wireless ECG monitoring system, along with a method of use for interactively detecting and analyzing a patient's cardiovascular activity. The present invention ECG monitoring system includes a processor, a memory for storing processed ECG signals, internally generated detection algorithms as well as uploaded new software applications. The present invention also includes a transceiver for wirelessly transmitting ECG signal data to outside computing devices. The present invention may also include an RFID reader for accessing patient database of information stored on RFID devices located in close proximity. The present invention ECG monitor also contains one or more software algorithms for detecting abnormal cardiovascular activities. The ECG processor continuously performs analysis on the recorded cardiovascular activity on real-time bases. When an abnormal event is detected, the present invention ECG device will automatically trigger an alarm and transmit wirelessly, to an outside computing device, the most recent history of patient's recorded data just prior to, and including the time during, the abnormality occurrence. The present invention ECG monitoring system then scrutinizes the recorded cardiovascular information leading to the abnormal event in order to further optimize its standard built-in algorithms for the patient being monitored. The ECG monitoring device can further access patient's past recorded history, located either on its local storage media or on outside remote computers via telemetry, to further customize the detection algorithms for each patient.

A novel and unique feature of the current invention is that it is reprogrammable, capable of uploading new detection algorithms wirelessly from outside computing devices for patient monitoring.

Another innovation of the present invention is that it is capable of uploading new software applications to help expand its monitoring and detection capabilities for ECG purposes as well as other monitoring needs such as EEG and EMG.

Another innovation of the present invention is that it is further capable of multitasking between a plurality of device-resident and uploaded software applications in parallel.

Another innovation of the present invention is that it is self-programmable and capable of analyzing the recorded heart waveforms including the events leading to any abnormal event and extracting parameters associated with the cardiovascular activity, including but not limited to the PR, QRS and ST intervals as well as the peak levels for R, S, P and T to generate newly customized detection algorithms for monitoring the said patient heart.

Another innovation of the present invention is its ability to adapt its monitoring system to each individual patient. Utilizing its built-in processing power, the present invention is capable of identifying the detection algorithms best suited for each individual patient's cardiovascular conditions. Those algorithms are then logged under the patient profile in the devices internal storage memory and utilized for all future monitoring purposes for the said patient.

It is another object of the present invention to access and analyze patient historical cardiovascular data located in the ECG device's local storage unit, to further improve its arrhythmia detection algorithms and detect trends in patient's heart condition.

It is another object of the present invention to utilize RFID communication to access database of patient information stored in an RFID device within close proximity to the device.

It is another object of the present invention to wirelessly access and analyze patient historical cardiovascular data located on remote computing devices to further customize its arrhythmia detection algorithms and identify trends in the patient's heart condition.

It is another object of the present invention to automatically adjust the device's resolution for detecting and recording patient heart waveforms with irregular and hard to analyze morphology.

It is another object of the present invention to automatically adjust the device's sampling rate to further improve the detection and analysis of the recorded patient cardiac waveforms with irregular and hard to analyze morphology.

It is another object of the present invention to automatically adjust the device's signal sensitivity level as well as signal gain control to further improve the detection and analysis of the recorded patient cardiac waveforms with irregular and hard to analyze morphology.

It is another object of the present invention to use leadwires connected to a plurality of electrode sensors attached to the person's body for acquiring the electrocardiograph data.

It is another object of the present invention to snap the ECG device into a docking bracket attached to a disposable patch with an adhesive surface with which it can attach to the patient's body.

It is another object of the present invention to snap the ECG device into a docking bracket attached to a re-usable patch with an adhesive surface with which it can attach to the patient's body.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
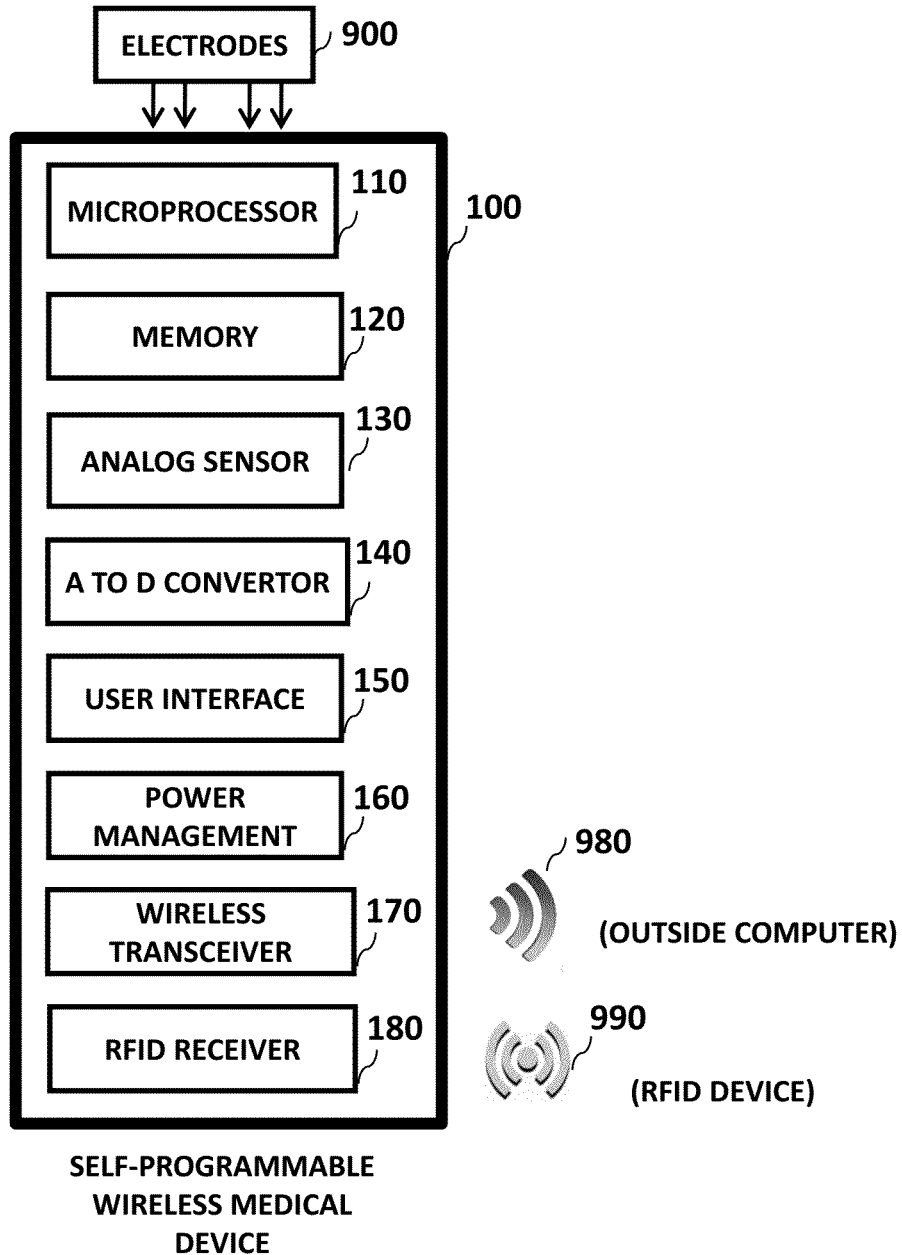
FIG. 1 is a block diagram of a preferred embodiment of the hardware architecture of the present invention Self-Programmable Wireless Medical Device.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

It should be noted that references to "an," "one," or "various" embodiments in this disclosure are not necessarily to the same embodiment, and such references contemplate more than one embodiment.

The present invention disclosed herein is a self-programmable ECG monitoring system and methods of use for analyzing the recorded information about a person's heart condition.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current Good Manufacturing Practice guidelines.

As used herein the term "Computing Device"" includes a desktop, laptop or tablet computer, as well as a mobile device.

"Telemetry" means the wireless transmission and reception of measured quantities for the purpose of remotely monitoring environmental conditions or equipment parameters.

"Software Application" means all the computer software that causes a computer to perform useful tasks beyond the running of the computer itself.

"PR interval" means the interval between the beginning of the P wave and the beginning of the QRS complex of an electrocardiogram that represents the time between the beginning of the contraction of the atria and the beginning of the contraction of the ventricles "QRS interval" means the interval from the beginning of the Q wave to the termination of the S wave, representing the time for ventricular depolarization.

"ST interval" means the interval immediately following the QRS complex which merges into the T wave.

"R level" means the amplitude of the initial upward deflection of the QRS complex, following the Q wave in the normal electrocardiogram and representing early depolarization of the ventricles.

"S level" means the amplitude of the downward deflection of the QRS complex following the R wave in the normal electrocardiogram and representing late depolarization of the ventricles.

"P level" means the amplitude of the deflection in the electrocardiogram produced by excitation of the atria.

"T level" means the amplitude of the deflection of the normal electrocardiogram following the QRS complex; it represents repolarization or recovery of the ventricles.

Disclosed herein and illustrated in FIGS. 1 through 10 is the present invention method and apparatus Self-Programmable Wireless ECG Device 1000.

The present invention 1000 has a hardware architecture 100, which is illustrated in FIG. 1, with reference to FIG. 1, wherein a plurality of electrodes 900 are placed on the patient's body, and are connected to the present invention 1000. The hardware architecture is contained within some type of appropriate housing, not shown, the electrodes 900 connect to the hardware architecture 100 via a series of wires. The present invention 1000 includes an Analog Sensor module 130 that receives the electrical signals from the electrodes 900 through the series of wires, and provides proper filtering and amplification circuitry to produce the desired waveform representing the patient's cardiovascular activity. The present invention includes an Analog to Digital (A to D) module 140 for digitizing the received analog waveforms. The current invention also includes a microprocessor 110 that provides the necessary computing power to process the digital data from the A to D module 140 and store the recorded information in the internal ECG Data Buffer 124a of the ECG Memory Module 120. The processor 110 also performs a series of algorithms stored in its Pre-stored Arrhythmia Algorithms memory 122a of the ECG Memory Module 120 for detecting arrhythmia and other abnormal heart activities. If abnormal heart activity is detected, the recorded information leading to the abnormal event is then saved in the Abnormal Event Data Buffer 124b of the Memory Module 120. Microprocessor 110 then extracts a series of ECG parameters from the recorded data and stores it in the ECG Parameter Buffer 126a of the Memory Module 120 and utilizes the saved ECG parameters to generate newly customized algorithms that are then saved in the Custom Generated Algorithms 122b of the Memory Module 120 as well as customized ECG parameters that are saved in the Custom Generated ECG Parameter Buffer 126b.

The microprocessor 110 is further capable of uploading historical recordings of the patient being monitored and saves them in the Uploaded Historical Recording 122c of the memory module 120. The microprocessor 110 further uploads historical ECG parameters and saves them in the Uploaded Historical ECG Parameters 126c of the memory module 120. The microprocessor 110 further uploads additional patient information and saves it in the Uploaded Patient Database 124c of the Memory Module 120. The microprocessor 110 further uploads additional software applications which are saved in the Uploaded Applications 128c of the Memory Module 120. The microprocessor 110 is further capable of multitasking between a plurality of device-resident and uploaded software applications in parallel.

Figure 9:
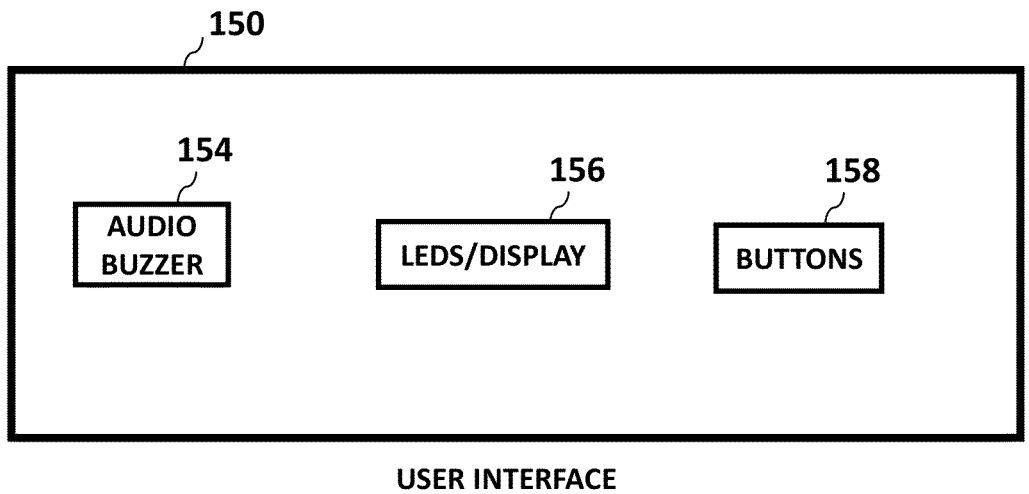
FIG. 9 is a block diagram of a preferred embodiment of the User Interface module the present invention Self-Programmable Wireless Medical Device.
Figure 10:
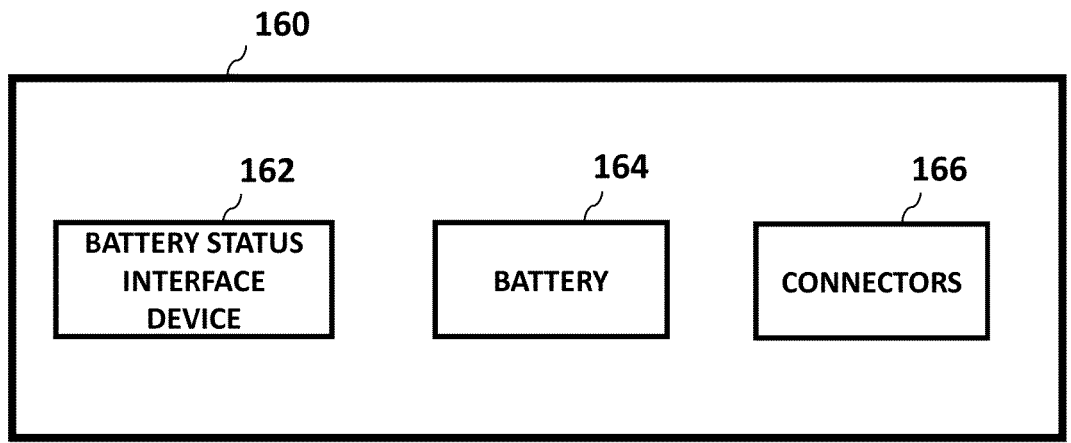
FIG. 10 is a block diagram of a preferred embodiment of the Power Management module the present invention Self-Programmable Wireless Medical Device.

Regarding FIG. 1, with further reference to FIGS. 9 and 10, a wireless transceiver 170 will communicate the recorded information to outside computing devices 980 via telemetry. Furthermore, if an abnormal event is detected in the patient's cardiovascular condition, the transceiver 170 wirelessly notifies outside computing devices and personnel of the patient's condition. User Interface Module 150 of the current invention 1000 includes a plurality of buttons and switches 158 for manually entering various commands to program the ECG device 1000 as required. An audio device 154 is available to prompt the patient of any abnormal heart activity. A number of light emitting diodes (LEDs) and a display unit 156 will also provide the operator with visual feedback of the status of the current invention. A rechargeable battery 164 of the Power Management Module 160 provides the power source for the ECG device 1000, and the supporting circuitry 162 provides feedback to the status of the battery-charge available. Connectors 166 provide access to an outside power source for charging the battery. RFID receiver 180 provides access to patient database stored in nearby RFID devices 990. The accessed information is then saved in the Uploaded Patient Database Buffer 124c of the Memory Module 120.

Figure 2:
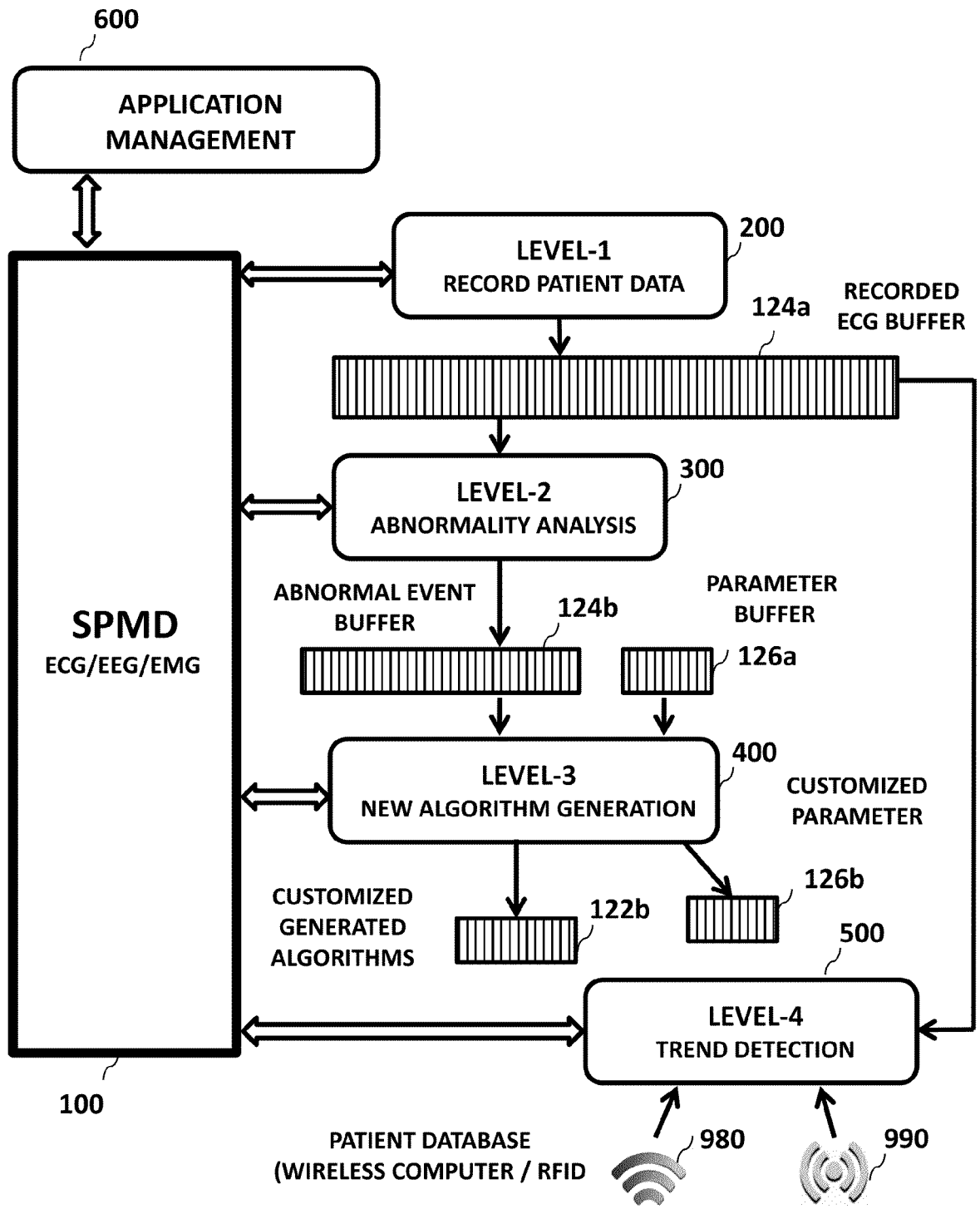
FIG. 2 is a preferred embodiment of the software flow diagram of the present invention Self-Programmable Wireless Medical Device.

Referring now to FIG. 2, there is shown a detail of Self-Programmable ECG Device Software Flow Diagram 2000. The initial program Application Management 600, which is shown in detail in FIG. 3, manages uploading of additional detection algorithms and software applications from outside computing devices 980 via telemetry and saves the uploaded information in the Uploaded Applications 128c.

Figure 4:
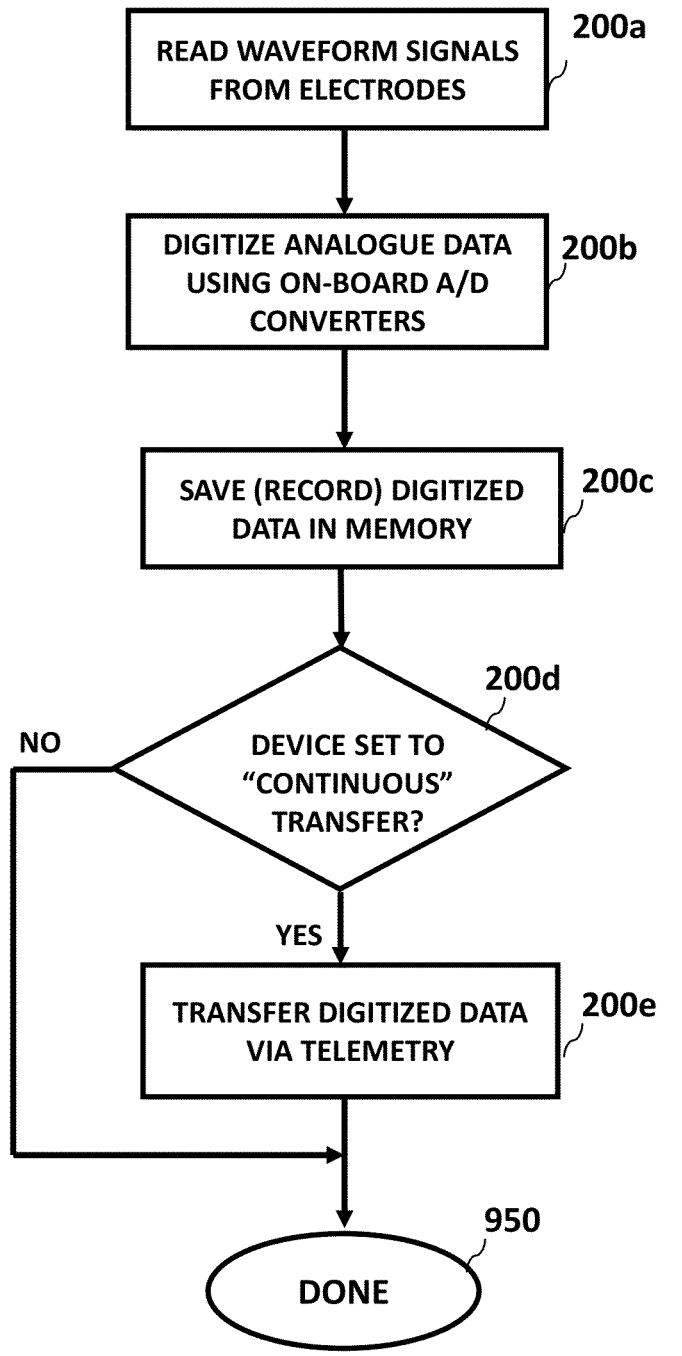
FIG. 4 is a preferred embodiment of the software flow diagram of the Level-1 Record ECG Data of the present invention Self-Programmable Wireless Medical Device.

The next program Level-1 Record ECG Data 200 obtains the electrical signals from the electrodes 900 and digitizes and stores the digital data in Recorded ECG Buffer 124a, which is shown in detail in FIG. 4.

Figure 5:
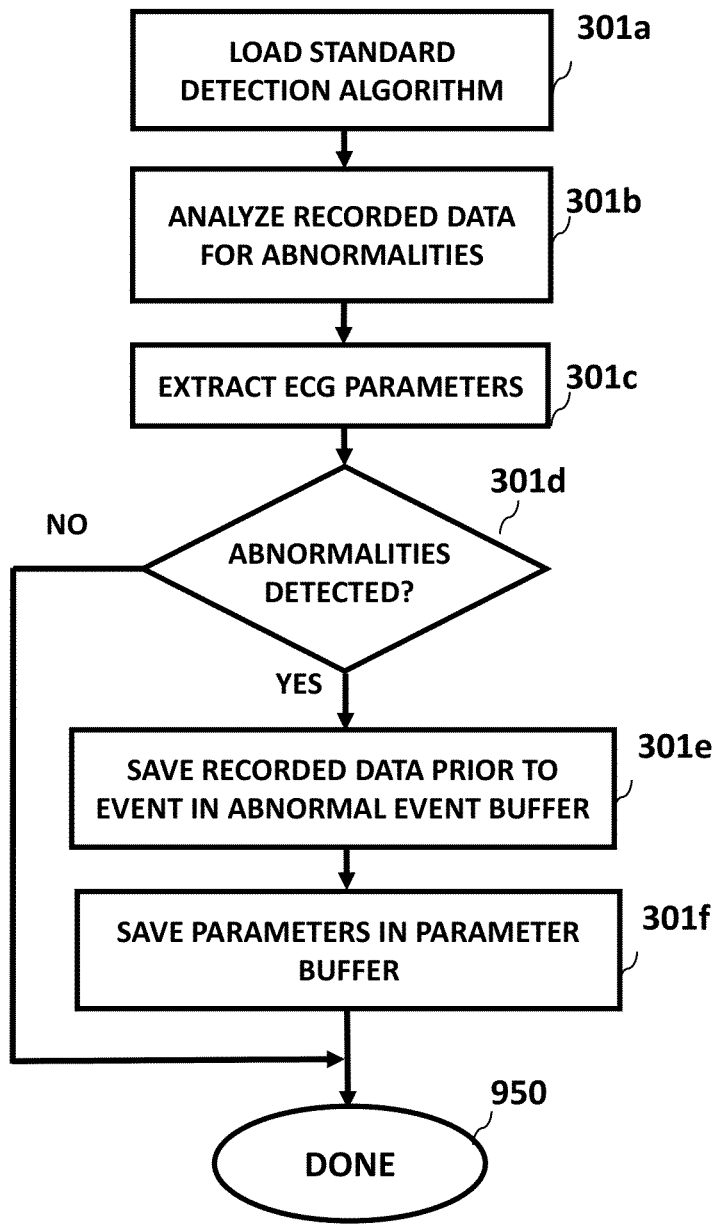
FIG. 5 is a preferred embodiment of the software flow diagram of the Level-2 Abnormality Analysis of the present invention Self-Programmable Wireless Medical Device.

The next program Level-2 Abnormality Analysis 300 scrutinizes the digitized ECG data for arrhythmia and other abnormal behavior, using pre-stored analysis algorithms, shown in detail in FIG. 5. In the event that an abnormality is detected, the patient's recent recorded history leading up to the abnormal event, is saved in the Abnormal Event Buffer 124b. The data saved in the Abnormal Event Buffer 124b is then further analyzed to help compute a series of ECG Parameters which are then saved in the ECG Parameter Buffer 126a, which is shown in detail in FIG. 5.

Figure 6:
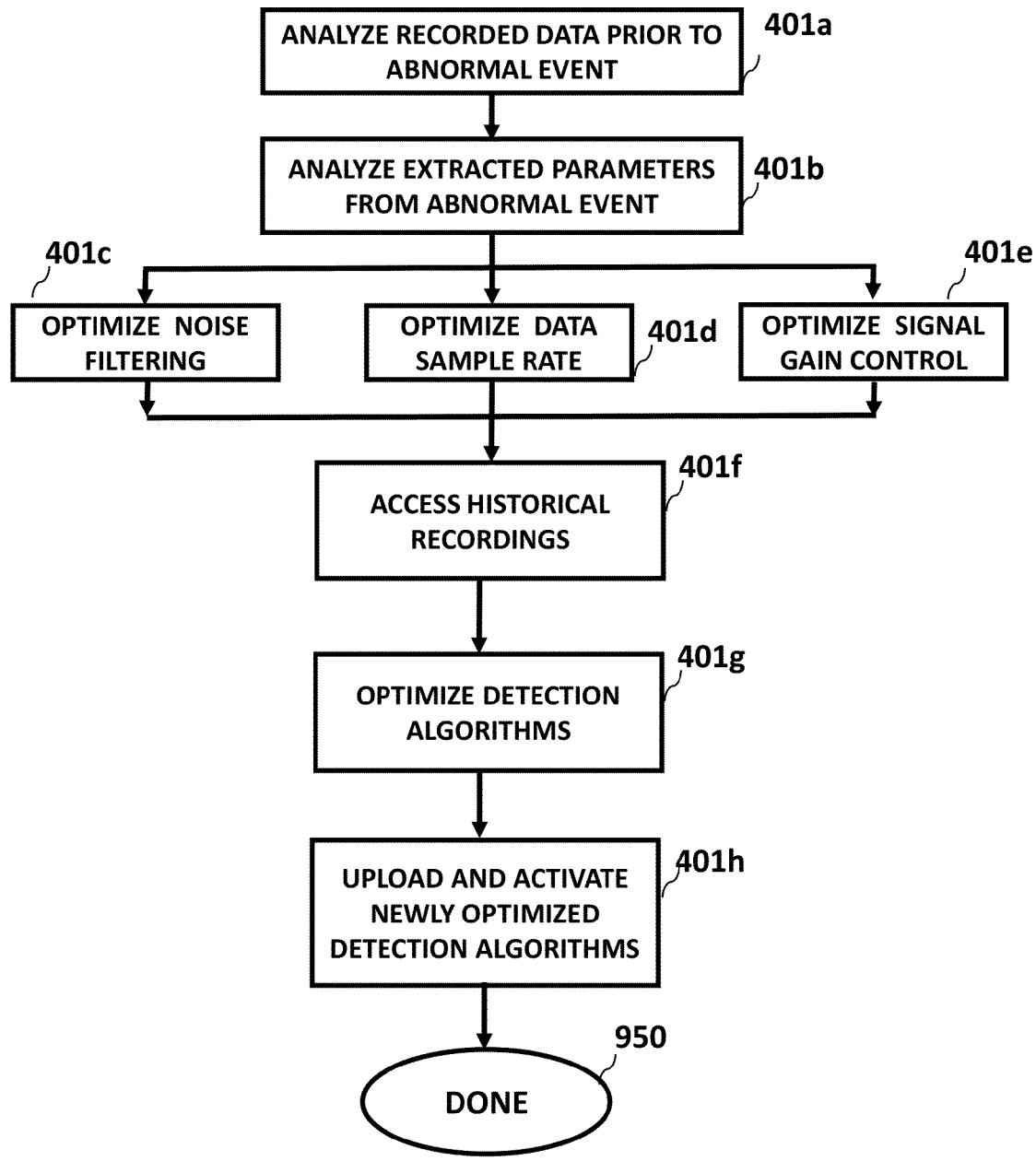
FIG. 6 is a preferred embodiment of the software flow diagram of the Level-3 New Algorithm Generation of the present invention Self-Programmable Wireless Medical Device.

Next, program Level-3 New Algorithm Generation 400, which is shown in detail in FIG. 6, further scrutinizes the data saved in the Abnormal Event Buffer 124b along with the parameters stored in the ECG Parameter Buffer 126a to develop a customized arrhythmia detection algorithm for the patient being monitored. The newly generated custom algorithm is then saved in the Custom Generated Algorithms 122b and activated for continuous monitoring of the said patient. Concurrently, program Level-3 New Algorithm Generation 400 scrutinizes the data saved in the Abnormal Event Buffer 124b along with the parameters stored in the ECG Parameter Buffer 126a to develop a series of customized ECG parameters. The newly developed custom ECG parameters are then saved in the Customized ECG Parameter 126b.

Figure 7:
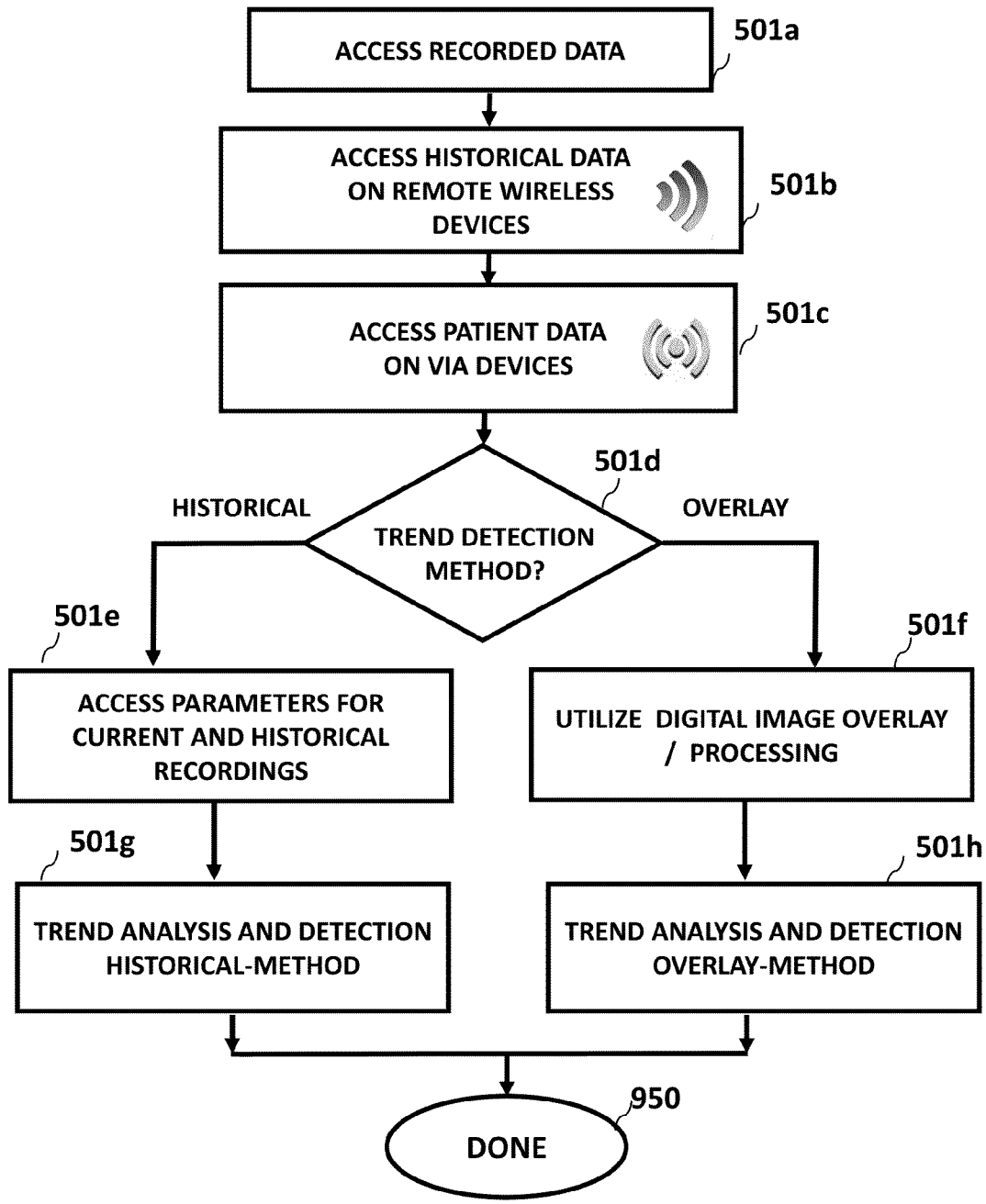
FIG. 7 is a preferred embodiment of the software flow diagram of the Level-4 Trend Detection of the present invention Self-Programmable Wireless Medical Device.

The next program, Level-4 Trend Detection 500, which is shown in detail in FIG. 7, accesses the digitized ECG data saved in the Recorded ECG Buffer 124a along with the patient's historical ECG recording on outside computing devices 980 via telemetry and the patient's database of information on nearby RFID devices 990 to detect possible "trends" in patient's cardiovascular performance.

Each of these software programming levels is described in further detail below.

Figure 3:
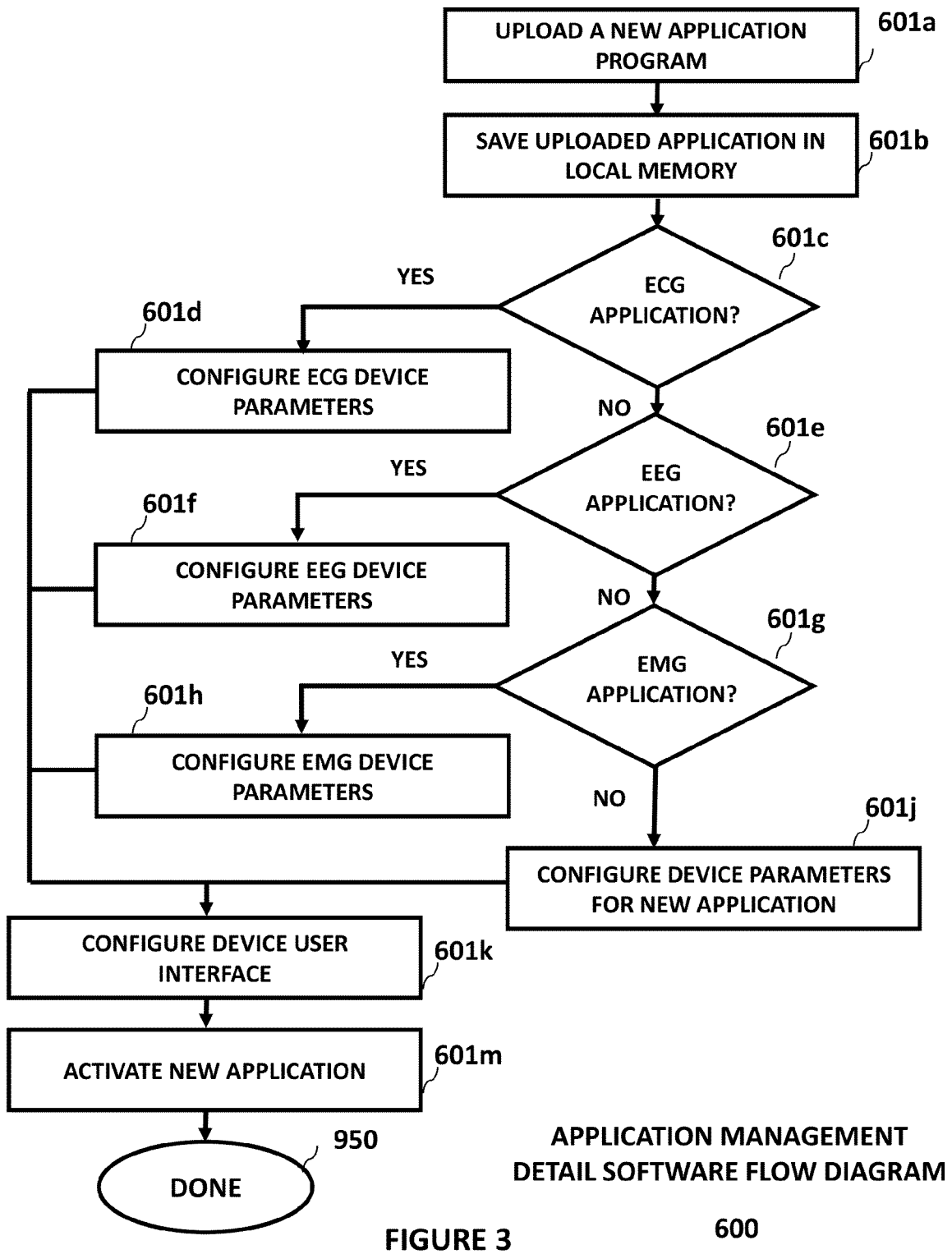
FIG. 3 is a flow chart diagram of a preferred embodiment of the software flow control of the Application Management of the present invention Self-Programmable Wireless Medical Device.

Referring now to FIG. 3, there is shown a detail of Application Management software flow diagram 600 of the present invention 1000. The Initial Task 601a, uploads new software applications from outside computing devices. Next, the uploaded applications are saved 601b in the Uploaded Applications storage area 128c of the Memory Module 120. The uploaded application type is then analyzed. If application type is electrocardiogram (ECG) 601c, then present invention 1000 is re-configured to operate as an ECG device using the new uploaded software application 601d. If application type is electroencephalogram (EEG) 601e, then present invention is re-configured to operate as an EEG device using the new uploaded software application 601f. If application type is electromyogram (EMG) 601g, then present invention 1000 is re-configured to operate as an EMG device using the new uploaded software application 601h. If any other application type is selected, then present invention 1000 is re-configured to operate for that application accordingly 601j. Next, present invention 1000 User Interface module 150 is re-configured for the newly uploaded application 601k. Finally, the newly uploaded application is activated 601m.

Referring now to FIG. 4, there is shown a detail of Level-1 Record ECG Data Software Flow Diagram 200. The Initial Task 200a obtains the electrical signals from the electrodes 900. It then implements Routine 200b, wherein it digitizes the obtained analog data using on-board A-D Converters 140 and stores them in the Recorded ECG Buffer 124a of the device's memory 120, in accordance with Routine 200c. Following that, the operation mode of the ECG is examined at 200d. In the event that the ECG device is set to "Continuous Transfer"

mode, then the digitized signals are also transmitted at 200e to outside wireless computing device(s) 980 via on-board wireless transceivers 170.

Referring now to FIG. 5, there is shown a detail of Level-2 Abnormality Analysis software flow diagram 300 which applies to the software task for analyzing the recorded data for arrhythmia and other cardiovascular abnormalities. ECG monitor 1000 contains a number of pre-loaded software algorithms in its Pre-stored Arrhythmia Algorithm storage area 122a. These algorithms are loaded at 301a. Next, the algorithms are used to scrutinize at 301b the patient's ECG signals for abnormalities. Following that, the next task of Level-2 Abnormality Analysis 300 further processes the patient's ECG signals in order to compute a series of ECG parameters 301c. In the event that abnormalities are detected 301d, the recorded data prior to the abnormal event is saved in the Abnormal Event Buffer 124b, in accordance with Routine 301e, and the computed series of ECG parameters are saved in ECG Parameter storage area 126a, in accordance with Routine 301f.

Referring now to FIG. 6, there is shown a detail of Level-3 New Algorithm Generation software flow diagram 400. The initial task 401a, analyzes recorded data prior to an abnormal event stored in the Abnormal Event Data Buffer 124b and is utilized to compute a new set of ECG parameters 401b. The above analysis is then further utilized to optimize the built-in algorithms of the ECG device 1000 for (a) improved noise filtering 401c, (b) improved data sample rate 401d and (c) optimized signal gain control 401e. Following that, the patient historical recordings are accessed 401f for further analysis. Using all of the above mentioned analyses and optimizations, a new customized algorithm is developed 401g, which is then saved in the Custom Generated Algorithm storage area 122b and activated for future analysis 401h.

Referring now to FIG. 7, there is shown a detail of Level-4 Trend Detection software flow diagram 500. The Initial Task 501a, accesses the patient's recorded data from Recorded ECG Data Buffer 124a. The next Task 501b, accesses the patient's historical recordings residing on outside computing devices 980 via telemetry. Following that, the patient's database of information is accessed 501c on RFID storage devices 990. Next, the status of trend method detection as set by the User Interface Module 150 of the ECG device 1000 is checked 501d. If trend detection method is set to "historical", then current and historical ECG parameters are accessed 501e and are analyzed to detect a trend in patient's cardiovascular health 501g. If however, trend detection method is set to "image overlay" then various images of the patient's current and historical cardiovascular recordings are superimposed and processed 501f to detect a trend in patient's cardiovascular health 501h.

Figure 8:
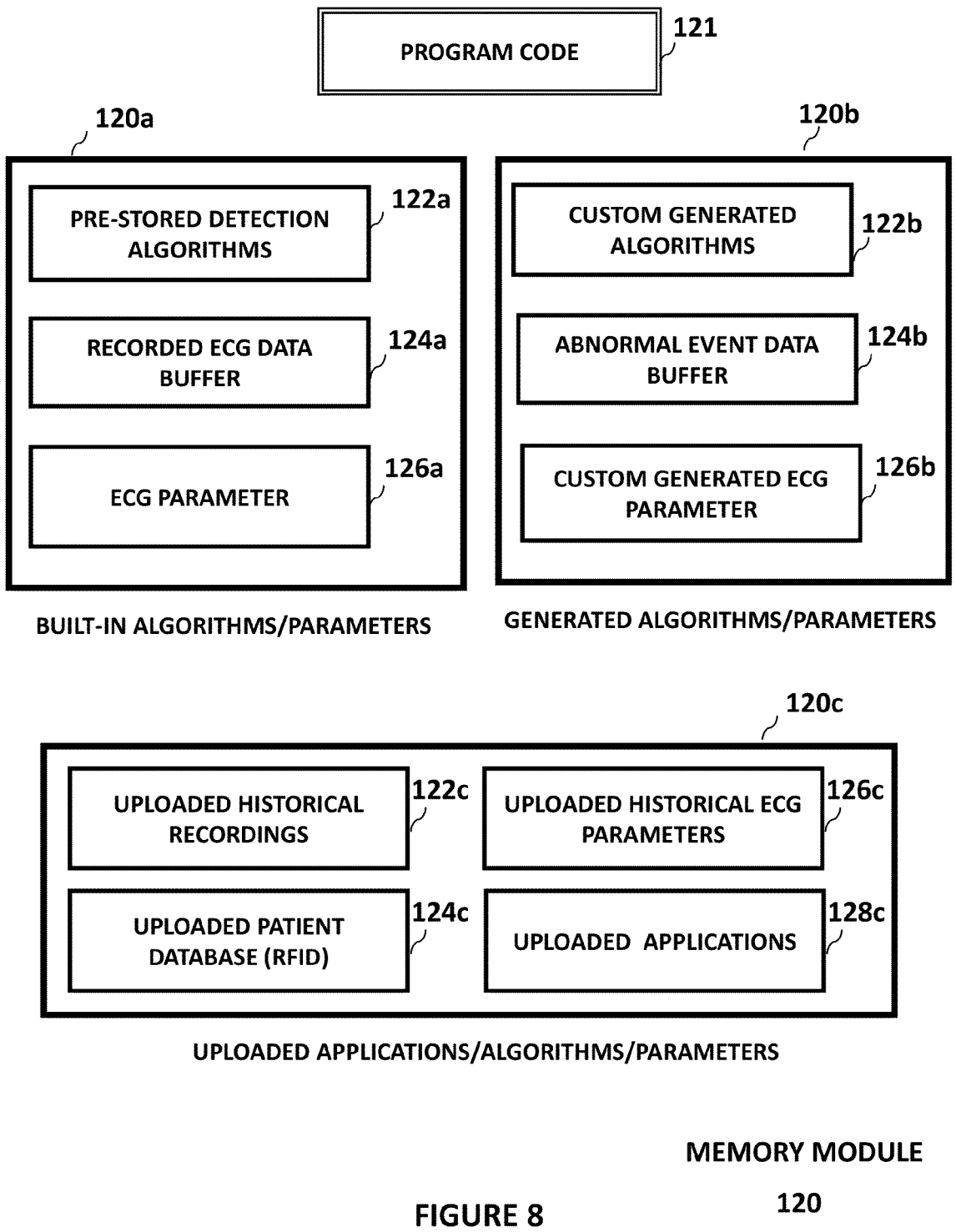
FIG. 8 is a block diagram of a preferred embodiment of the memory module of the present invention Self-Programmable Wireless Medical Device.

Referring now to FIG. 8, there is shown a detail of the Memory Module 120 of the ECG device 1000. The innovative Memory Module 120 is comprised of multiple storage compartments; the preferred embodiment illustrates four such compartments. This superior Memory Module structure enables the current invention 1000 to simultaneously support (a) operating software code or main operating code for the device, (b) built-in detection algorithms, (c) self-generated custom algorithms, and (d) uploaded algorithms and software applications. Each of these storage compartments is described in further detail below.

The Storage Compartment 121 of the Memory Module 120 contains the Main Program Code of the ECG device 1000.

The Storage Compartment 120a of the Memory Module 120 contains built-in algorithms as well as the recorded patient information. The Pre-stored Detection Algorithms area 122a of the Storage Compartment 120a contains various algorithms initially loaded into the ECG device 1000 for detecting arrhythmia and other abnormal heart activities. Recorded cardiac information is continuously stored in the Recorded ECG Data Buffer 124a of the Storage Compartment 120a. ECG parameters computed from the recorded cardiac information are stored in the ECG Parameter area 126a of the Storage Compartment 120a.

The Storage Compartment 120b of the Memory Module 120 contains the newly generated detection algorithms by the ECG device 1000 as well as the recorded patient information leading to the abnormal events. The Custom Generated Algorithms area 122b of the Storage Compartment 120b contains internally generated algorithms for detecting arrhythmia and other abnormal cardiac activities. Recorded cardiac information leading to abnormal events is stored in the Abnormal Event Data Buffer 124b of the Storage Compartment 120b. Internally computed customized ECG parameters are then stored in the Custom Generated ECG parameter area 126b of the Storage Compartment 120b.

The Storage Compartment 120c of the Memory Module 120 contains the patient historical recordings and database, as well as new software applications uploaded into the ECG device 1000. Historical patient cardiac recordings uploaded from outside computing devices are saved in the Uploaded Historical Recordings area 122c of the Storage Compartment 120c. Patient database accessed from close proximity from outside RFID devices are saved in the Uploaded Patient Database area 124c of the Storage Compartment 120c. Historical ECG parameters uploaded from outside computing devices are saved in the Uploaded Historical ECG Parameters area 126c of the Storage Compartment 120c. New software applications uploaded from local or remote outside computing devices are saved in the Uploaded Applications area 128c of the Storage Compartment 120c.

Referring now to FIG. 9, there is shown a detail of the User Interface Module 150 of the current invention ECG Device 1000. The Microprocessor 110 provides the means for the patient or the doctor to reprogram the ECG device 1000 through a series of buttons and switches 158. In the event of the detection of an abnormality, an audio feedback 154 and visual feedback and communication is provided via the LEDs (light emitting diodes) and display 156.

Referring now to FIG. 10, there is shown a detail of The Power Management Module 160 of the ECG device 1000 that contains a battery device 164 and the supporting battery status circuitry 162 and connectors 166.

What is claimed is:

1. A portable medical device monitoring system for a patient, the monitoring system comprising:
   a. a plurality of electrodes placed on configured for the patient's body for sensing electrical signals;
   b. a processor to process and digitize the recorded signals, wherein the processor is capable of multi-tasking by simultaneously performing one or more software applications;
   c. a transceiver for wirelessly transmitting the processed signals to outside computing devices and receiving additional detection algorithms and patient historical recordings;
   d. a memory further comprised of at least one module, said memory stores the processed signals, stores one or more pre-programmed algorithm software for detecting abnormal activities, stores custom developed algorithms and software applications downloaded from outside computing devices;

e. wherein the device contains one or more detection algorithms in its memory;

f. wherein the device is re-programmable and loads and performs additional detection algorithms;

g. wherein the device is self-programmable and analyzes the patient's recorded activities leading to an abnormal event and optimizes its internal detection algorithms and develops new customized algorithms which is then saved in the Custom Generated Algorithm storage area and activates those newly developed algorithms for continuous monitoring of the said patient;

h. wherein the device uploads additional software applications from outside computing devices with which it re-programs itself to configure itself for additional applications and medical monitoring of the patient; and i. wherein the device uploads additional software applications from outside computing devices with which it re-programs itself to configure itself for additional applications and medical monitoring of the patient.

2. The monitoring system of claim 1, wherein the uploaded software application configures the device to be used as an electrocardiogram (ECG) device.

3. The monitoring system of claim 1, wherein the uploaded software application configures the device to be used as an electroencephalogram (EEG) device.

4. The monitoring system of claim 1, wherein the software application to be uploaded configures the device to be used as an electromyogram (EMG) device.

5. The monitoring system of claim 1, wherein the device detects trends in the patient's health conditions by utilizing image processing and image overly techniques to compare and correlate the patient's recorded health data with historical recordings.

6. The monitoring system of claim 1, wherein the device is contained in a watertight sealed case with only electrical contacts on the outside of the case.

7. The monitoring system of claim 1, wherein the device utilizes a RFID reader to access historical recorded data on RFID devices.

8. A portable ECG monitoring system for a patient, the ECG monitoring system comprising:

a. a plurality of electrodes placed on configured for the patient's body for sensing ECG signals;

b. a processor to process and digitize the recorded ECG signals, wherein the processor is capable of multi-tasking by simultaneously performing one or more software applications;

c. a transceiver for wirelessly transmitting the processed ECG signals to outside computing devices and receiving additional detection algorithms and patient historical cardiovascular recordings;

d. a memory further comprised of at least one module, said memory stores the processed ECG signals, stores one or more pre-programmed arrhythmia detection algorithms for detecting abnormal cardiovascular activities, stores custom developed algorithms and software applications downloaded from outside computing devices;

e. wherein the device contains one or more arrhythmia detection algorithms in its memory;

f. wherein the device is re-programmable and loads and performs additional detection algorithms;

g. wherein the device is self-programmable and analyzes the patient's recorded activities leading to an abnormal event and optimizes its internal detection algorithms and develops new customized algorithms which is then saved in the Custom Generated Algorithm storage area and activates those newly developed algorithms for continuous monitoring of the said patient; and h. wherein the device uploads additional software applications from outside computing devices with which it re-programs itself to configure itself for additional applications and medical monitoring of the patient.

9. The ECG monitoring system of claim 8, wherein the uploaded software application configures the device to be used as an electroencephalogram (EEG) device.

10. The ECG monitoring system of claim 8, wherein the uploaded software application configures the device to be used as an electromyogram (EMG) device.

11. The ECG monitoring system of claim 8, wherein the device analyzes the patient's recorded heart waveforms and computes parameters associated with the cardiovascular activity, such as the PR, QRS and ST intervals, and the peak levels for R, S, P and T to generate newly customized detection algorithms for monitoring the said patient's heart.

12. The ECG monitoring system of claim 8, wherein the device detects trends in the patient's cardiac conditions by utilizing image processing and image overly techniques to compare and correlate recorded cardiovascular data with historical recordings.

13. The ECG monitoring system of claim 8, wherein the device utilizes a RFID reader to access historical recorded data on RFID devices.

14. The ECG monitoring system of claim 8, wherein the device affixes to a patch.

15. The ECG monitoring system of claim 14, wherein the device affixes patch is disposable.

16. The ECG monitoring system of claim 8, wherein the device is contained in a watertight sealed case with only electrical contacts on the outside of the case.

* * * * *